United States Patent
Mubima

(10) Patent No.: US 9,234,156 B2
(45) Date of Patent: Jan. 12, 2016

(54) LOW-COLOR ESTER COMPOSITIONS AND METHODS OF MAKING AND USING THE SAME

(71) Applicant: Elevance Renewable Sciences, Inc., Woodridge, IL (US)

(72) Inventor: Daniel Mubima, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/705,772

(22) Filed: May 6, 2015

(65) Prior Publication Data

US 2015/0336873 A1  Nov. 26, 2015

Related U.S. Application Data

(60) Provisional application No. 62/001,172, filed on May 21, 2014.

(51) Int. Cl.
*C11B 3/08* (2006.01)
*C11B 3/02* (2006.01)
*C07C 67/60* (2006.01)

(52) U.S. Cl.
CPC ... *C11B 3/08* (2013.01); *C11B 3/02* (2013.01); *C07C 67/60* (2013.01)

(58) Field of Classification Search
None
See application file for complete search history.

(56) References Cited

U.S. PATENT DOCUMENTS

| 4,325,883 A * | 4/1982 | Jones | C11B 3/08 554/182 |
|---|---|---|---|
| 5,401,862 A | 3/1995 | Gonus et al. | |
| 5,902,890 A | 5/1999 | Nitsche et al. | |
| 7,544,822 B2 | 6/2009 | Ho | |

FOREIGN PATENT DOCUMENTS

| EP | 0459172 | 9/1995 | |
|---|---|---|---|
| EP | 0459172 B1 * | 9/1995 | C07H 13/06 |
| WO | 2006/034556 | 4/2006 | |

OTHER PUBLICATIONS

International Search Report for PCT App. No. PCT/US2015/029516, dated Jul. 27, 2015.

* cited by examiner

*Primary Examiner* — Yate K Cutliff
(74) *Attorney, Agent, or Firm* — Robert S. Dailey

(57) ABSTRACT

Low-color ester compositions and methods of making low-color ester compositions are generally disclosed. In certain embodiments, methods of making low-color ester compositions from a biorefinery bottoms stream are disclosed. In some other embodiments, methods for recovering esters of 1,18-octadecanedioic acid are disclosed.

20 Claims, 4 Drawing Sheets

100

101 Providing a fatty acid ester composition

102 Chemically treating the fatty acid ester composition even though the pot bottoms can also include other
LOW-COLOR ESTER COMPOSITIONS AND METHODS OF MAKING AND USING THE SAME

CROSS-REFERENCE TO RELATED APPLICATIONS

The present application claims the benefit of priority of U.S. Provisional Application 62/001,172, filed May 21, 2014, which is hereby incorporated by reference as though set forth herein in its entirety.

TECHNICAL FIELD

Low-color ester compositions and methods of making low-color ester compositions are generally disclosed. In certain embodiments, methods of making low-color ester compositions from a biorefinery bottoms stream are disclosed. In some other embodiments, methods for recovering esters of 1,18-octadecanedioic acid are disclosed.

BACKGROUND

Natural oils can be refined, e.g., in a biorefinery, by cross-metathesizing the glyceride or a transesterified derivative thereof with a short-chain olefin. When the short-chain olefin is a $C_{2-4}$ olefin, the refining process yields a predominant amount of $C_{10-12}$ esters and olefins. The product stream contains a variety of other compounds, however. Many of these compounds are relatively non-volatile and cannot be easily separated by fractional distillation. In some instances, these materials can remain in the distillation pot. These materials can be referred to as the "pot bottoms" or "bottoms" from the fractionating process. The pot bottoms can also include other waste materials from the metathesis process, such as heavy metals and other compounds that may be present in the oil (e.g., colored impurities).

In many instances, this bottoms stream may contain certain compounds or combinations of compounds that have economic value because of their utility in certain applications. Therefore, it may be desirable to carry out various treatments on the bottoms stream to yield compounds or compositions that can be used in various applications.

In many instances, the bottoms stream can contain certain colored impurities, such as carotenes, which can interfere with the ultimate utility of the composition. It can be desirable to treat the composition chemically to decolorize the composition, e.g., be chemically transforming the colored species to compounds that are not colored. Some methods of decolorizing the composition may also react with the valuable materials in the composition and thereby decrease the value of the bottoms stream. In the context of refining a natural oil, the bottoms stream contains some mixture of olefins and esters (including both mono-esters and di-esters). Therefore, it may be desirable to decolorize the composition in a manner that does not react with these compounds in a way that substantially lowers their economic value. In some instances, a mixture of chromic and sulfuric acids can be used. But this has certain disadvantages, primarily related to the use and disposal of hexavalent chromium. Therefore, there is a need to develop additional ways of decolorizing a biorefinery bottoms stream, so as to reduce the color without substantially affecting the value of the olefins and/or esters in the stream.

SUMMARY

In a first aspect, the disclosure provides methods of removing colored impurities from a fatty acid ester composition, the method including: providing a fatty acid ester composition, the composition comprising (a) one or more esters of monobasic fatty acids, (b) one or more esters of dibasic fatty acids, and (c) one or more chromophoric impurities; and chemically treating the fatty acid ester composition to reduce the concentration of at least one of the one or more chromophoric impurities. In some embodiments, the method includes separating at least a portion of at least one of the one or more esters of dibasic fatty acids. In some such embodiments, the separated ester of a dibasic acid is an alkyl ester (e.g., a dimethyl diester) of 1,18-octadecanedioic acid.

In a second aspect, the disclosure provides low-color fatty acid ester compositions, the compositions including: one or more esters of monobasic fatty acids; and one or more esters of dibasic fatty acids; wherein the composition is substantially free of chromophoric impurities. In some embodiments, the composition is derived from the metathesis of a natural oil. In some such embodiments, the composition is a bottoms stream from the metathesis of a natural oil in a biorefinery.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
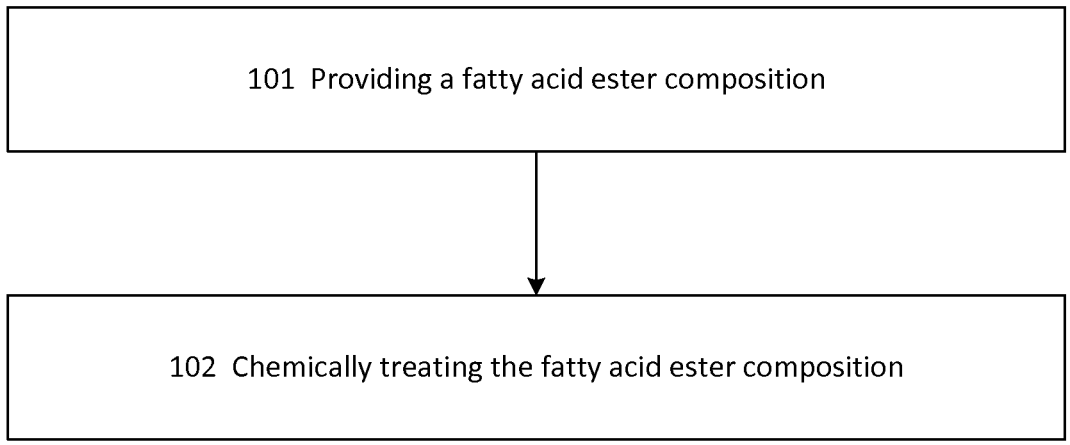
FIG. 1 shows a non-limiting example of a method of removing colored impurities from a fatty acid ester composition, which includes providing a fatty acid ester composition, and chemically treating the fatty acid ester composition to reduce the concentration of at least one of the one or more chromophoric impurities.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$," which refers to a group of compound having z carbon atoms; and "$C_{x-y}$," which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, iso-propyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O-]$_x$-alkyl, or -[-(alkylene)-O-]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively. Non-limiting examples include "oxyalkenyl" or "oxyalkenylene" groups, which are groups of the following formulas: —[—(R$^f$)—O—]$_x$—R$^g$, or —[—(R$^f$)—O—]$_x$—R$^h$—, respectively, where x is 1 or more, such as 1, 2, 3, 4, 5, 6, 7, or 8, and R$^f$, R$^g$, and R$^h$ are independently alkyl/alkylene or alkenyl/alkenylene groups, provided that each such "oxyalkenyl" or "oxyalkenylene" group contains at least one carbon-carbon double bond.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.
Methods of Chemically Treating a Composition to Remove Chromophoric Impurities In certain aspects, the disclosure provides methods of removing colored impurities from a fatty acid ester composition. In some embodiments, the method includes providing a fatty acid ester composition, which includes: (a) one or more esters of monobasic fatty acids; (b) one or more esters of dibasic fatty acids; and (c) one or more chromophoric (or colored) impurities.

As used herein, the term "providing" is to be interpreted broadly to include, without limitation, any making, preparing, delivering, receiving, or manipulating the fatty acid ester composition. In the same way, the term "fatty acid" is also to be interpreted broadly to include any aliphatic hydrocarbyl group, which may optionally be unsaturated, having one or more carboxylic acid groups. In some embodiments, the fatty acid has from 6 to 36 carbon atoms, or from 8 to 36 carbon atoms, or from 10 to 36 carbon atoms. In the same way, the term "fatty acid ester" refers to a fatty acid where at least one of its one or more carboxylic groups is esterified, i.e., where the hydrogen atom of the acid moiety (—COOH) is replaced by an organic group, such as a hydrocarbyl group.

In some embodiments, the fatty acid ester composition includes one or more esters of monobasic fatty acids. In some embodiments, the one or more esters of monobasic fatty acids are compounds of formula (I):

$$R^1—C(=O)—O—R^2 \qquad (I)$$

wherein $R^1$ is $C_{6-36}$ alkyl or $C_{6-36}$ alkenyl; and $R^2$ is $C_{1-24}$ alkyl, $C_{2-24}$ alkenyl, $C_{1-24}$ heteroalkyl, or $C_{2-24}$ heteroalkenyl, each of which is optionally substituted with one or more hydroxyl groups.

In some embodiments, $R^1$ is $C_{6-36}$ alkyl or $C_{6-36}$ alkenyl. In some embodiments, $R^1$ is $C_{9-27}$ alkyl or $C_{9-27}$ alkenyl. In some embodiments, $R^1$ is $C_{9-25}$ alkyl or $C_{9-25}$ alkenyl. In some embodiments, $R^1$ is $C_{9-23}$ alkyl or $C_{9-23}$ alkenyl. In some such embodiments, $R^1$ is —(CH$_2$)$_{14}$—CH$_3$, —(CH$_2$)$_{16}$—CH$_3$, —(CH$_2$)$_{18}$—CH$_3$, —(CH$_2$)$_{19}$—CH$_3$, —(CH$_2$)$_{22}$—CH$_3$, or —(CH$_2$)$_7$—CH=CH—(CH$_2$)$_7$—CH$_3$.

In some embodiments, $R^2$ is $C_{1-12}$ alkyl or $C_{1-12}$ oxyalkyl, each of which is optionally substituted with one or more hydroxyl groups. In some embodiments, $R^2$ is $C_{1-6}$ alkyl, which is optionally substituted with one or more hydroxyl groups. In some embodiments, $R^2$ is methyl, ethyl, or isopropyl. In some embodiments, $R^2$ is methyl. In some other embodiments, $R^2$ is a glyceryl group.

In some other embodiments, the one or more esters of monobasic fatty acids are esters of $C_{12-24}$ monobasic fatty acids. In some embodiments, the one or more esters of monobasic fatty acids are esters of $C_{14-21}$ monobasic fatty acids. In some embodiments, the one or more esters of monobasic fatty acids are esters of palmitic acid, stearic acid, oleic acid, arachidic acid, heneicosylic acid, lignoceric acid, or mixtures thereof. In some embodiments, the one or more esters of monobasic fatty acids are esters of palmitic acid, stearic acid, or mixtures thereof.

In the aforementioned esters, any suitable alcoholic moiety can be used, including heteroalkyl groups, such as oxyalkyl and glycerides. In some embodiments, the one or more esters of monobasic fatty acids are glyceryl esters of monobasic fatty acids. In some such embodiments, the glyceryl groups of the glyceryl esters of monobasic fatty acids are monoglycerides, diglycerides, triglycerides, or mixtures thereof. In some other embodiments, the one or more esters of monobasic fatty acids are $C_{1-12}$ alkyl esters of monobasic fatty acids. In some such embodiments, the $C_{1-12}$ alkyl esters of monobasic fatty acids are methyl esters of monobasic fatty acids, ethyl esters of monobasic fatty acids, isopropyl esters of monobasic fatty acids, or mixtures thereof. In some embodiments, the $C_{1-12}$ alkyl esters of monobasic fatty acids are methyl esters of monobasic fatty acids.

In some embodiments, the fatty acid ester composition includes one or more esters of dibasic fatty acids. In some embodiments, the one or more esters of dibasic fatty acids are compounds of formula (II):

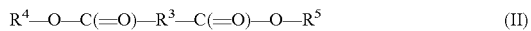

$$R^4-O-C(=O)-R^3-C(=O)-O-R^5 \qquad (II)$$

wherein $R^3$ is $C_{6-36}$ alkylene or $C_{6-36}$ alkenylene; and $R^4$ and $R^5$ are independently $C_{1-24}$ alkyl, $C_{2-24}$ alkenyl, $C_{1-24}$ heteroalkyl, or $C_{2-24}$ heteroalkenyl, each of which is optionally substituted with one or more hydroxyl groups.

In some embodiments, $R^3$ is $C_{6-36}$ alkylene or $C_{6-36}$ alkenylene. In some embodiments, $R^3$ is $C_{8-26}$ alkylene or $C_{8-26}$ alkenylene. In some embodiments, $R^3$ is $C_{8-24}$ alkylene or $C_{8-24}$ alkenylene. In some embodiments, $R^3$ is $C_{8-22}$ alkylene or $C_{8-22}$ alkenylene. In some such embodiments, $R^3$ is $-(CH_2)_{16}-$, $-(CH_2)_{18}-$, or $-(CH_2)_{19}-$.

In some embodiments, $R^4$ and $R^5$ are independently $C_{1-12}$ alkyl or $C_{1-12}$ oxyalkyl, each of which is optionally substituted with one or more hydroxyl groups. In some embodiments, $R^4$ and $R^5$ are independently $C_{1-6}$ alkyl, which is optionally substituted with one or more hydroxyl groups. In some embodiments, $R^4$ and $R^5$ are independently methyl, ethyl, or isopropyl. In some embodiments, $R^4$ and $R^5$ are methyl. In some other embodiments, at least one of $R^4$ and $R^5$ are independently glyceryl groups.

In some other embodiments, the one or more esters of dibasic fatty acids are esters of $C_{12-24}$ dibasic fatty acids. In some embodiments, the one or more esters of dibasic fatty acids are esters of $C_{14-21}$ dibasic fatty acids. In some embodiments, the one or more esters of dibasic fatty acids are esters of octadecanedioic acid, eicosanedioic acid, heneicosanedioic acid, or mixtures thereof. In some embodiments, the one or more esters of dibasic fatty acids are esters of octadecanedioic acid, heneicosanedioic acid, or mixtures thereof.

In some further embodiments of the aforementioned embodiments, the one or more esters of dibasic fatty acids are one or more monoesters of dibasic fatty acids, one or more diesters of dibasic fatty acids, or mixtures thereof. In some such embodiments, the one or more esters of dibasic fatty acids are one or more diesters of dibasic fatty acids. In some embodiments, the one or more diesters of dibasic fatty acids are glyceryl diesters of dibasic fatty acids. In some such embodiments, the glyceryl groups of the glyceryl diesters of dibasic fatty acids are monoglycerides, diglycerides, triglycerides, or mixtures thereof. In some other embodiments, the one or more diesters of dibasic fatty acids are $C_{1-12}$ alkyl diesters of dibasic fatty acids. In some such embodiments, the $C_{1-12}$ alkyl diesters of dibasic fatty acids are methyl diesters of dibasic fatty acids, ethyl diesters of dibasic fatty acids, isopropyl diesters of dibasic fatty acids, or mixtures thereof. In some embodiments, the $C_{1-12}$ alkyl diesters of dibasic fatty acids are methyl diesters of dibasic fatty acids.

In some embodiments, the fatty acid ester composition contains esters of monobasic acids and esters of dibasic acids. In such embodiments, the composition can have any suitable ratio of esters of monobasic acids to esters of dibasic acids. In some embodiments, the weight-to-weight ratio the one or more monobasic fatty acids to the one or more dibasic fatty acids ranges from 1:10 to 10:1, or from 1:5 to 5:1, or from 1:3 to 3:1, or from 1:2 to 2:1.

The fatty acid ester composition can also include certain impurities. For example, in instances where the fatty acid ester composition is derived from a natural oil, the composition can contain certain quantities of colored impurities (also referred to as chromophoric impurities) which are present in the plant or animal from which the oil is derived.

The fatty acid ester composition can include any chromophoric impurities that are commonly found in animal or plant sources. For example, in some embodiments the chromophoric impurity is a tetraterpenoid, such as a carotenoid. In some embodiments, the chromophoric impurity is a xanthophyll, a carotene, or a mixture thereof. In some embodiments, the chromophoric impurity is a carotene, such as alpha-carotene, beta-carotene, gamma-carotene, delta-carotene, epsilon-carotene, zeta-carotene, or a mixture thereof. In some embodiments, the chromophoric impurity is beta-carotene.

In some embodiments, the methods disclosed herein include chemically treating the fatty acid ester composition to reduce the concentration of at least one of the one or more chromophoric impurities. In some embodiments, this includes contacting the fatty acid ester composition with a decolorizing composition. In some embodiments, the decolorizing composition is an aqueous composition. In some embodiments, the decolorizing composition includes one or more oxidizing agents. In some embodiments, the one or more oxidizing agents are anionic oxidizing agents. In some embodiments, the decolorizing composition is an aqueous composition having a pH of at least 5, or at least 6, or at least 7. In some embodiments, the decolorizing composition is an aqueous composition having a pH ranging from 5 to 14, or from 6 to 13, or from 6 to 12, or from 6 to 11, or from 7 to 10. In some such embodiments, the decolorizing composition includes chlorite ($ClO_2^-$) anion. In some embodiments, the decolorizing composition includes persulfate ($S_2O_8^{2-}$) anion. In some embodiments, the decolorizing composition includes chlorite ($ClO_2^-$) anion and persulfate ($S_2O_8^{2-}$) anion. The anions can be included in the decolorizing composition in any suitable form. In some embodiments, the anions are included in the decolorizing composition as alkali metal salts, such as sodium chlorite and sodium persulfate. In such embodiments, any suitable relative amounts of sodium chlorite and sodium persulfate can be used. In some such embodiments, the weight-to-weight ratio of sodium chlorite to sodium persulfate in the decolorizing composition ranges from 1:10 to 10:1, or from 1:5 to 5:1, or from 1:3 to 3:1. Further, the any suitable concentrations of chlorite and persulfate can be used to prepare the decolorizing composition. For example, in some embodiments, the concentration of persulfate in the decolorizing composition ranges from 0.1 M to 1.0 M, or from 0.1 M to 0.8 M. In some embodiments, the concentration of chlorite in the decolorizing composition ranges from 0.2 M to 2.0 M, or from 0.4 M to 1.6 M.

In some embodiments, the aforementioned chemical treatment reduces the concentration of at least one of the one or more chromophoric impurities in the fatty acid ester composition. For example, in embodiments where the one or more chromophoric impurities include carotenes, the chemical treatment reduces the concentration of carotenes in the fatty acid ester composition. In some such embodiments, the chemically treating reduces the concentration of carotenes in the fatty acid ester composition by at least 20%, or at least 30%, at least 40%, or at least 50%, or at least 60%, or at least 70%, or at least 80%, or at least 90%, or at least 95%, or at least 97%, or at least 99%, based on the original concentration of carotenes in the fatty acid ester composition. As another example, in embodiments where the one or more chromophoric impurities includes beta-carotene, the chemical treatment reduces the concentration of beta-carotene in the fatty acid ester composition. In some such embodiments, the chemically treating reduces the concentration of beta-carotene in the fatty acid ester composition by at least 20%, or at least 30%, at least 40%, or at least 50%, or at least 60%, or at least 70%, or at least 80%, or at least 90%, or at least 95%, or at least 97%, or at least 99%, based on the original concentration of beta-carotene in the fatty acid ester composition.

In some instances, color can be measured using the American Oil Chemists Society (AOCS) Tintometer Scale using AOCS Official Method Cc 13b-45. When such measurements are referred to herein, they refer to their recordation using a LOVIBOND PFX995 Tintometer. The color of a sample, such as a fatty acid ester composition, measured using this method provides a value on the AOCS-Tintometer Red Scale (which runs from 0.1 to 20.0) and a value on the AOCS-Tintometer Yellow Scale which runs from 0.1 to 70.0).

In some embodiments, the aforementioned chemical treatment reduces the color of the fatty acid ester composition on the AOCS-Tintometer Red Scale. In some such embodiments, the chemical treatment reduces the color of the fatty acid ester composition such that the composition has a color value on the AOCS-Tintometer Red Scale of no more than 10.0, or no more than 9.0, or no more than 7.6, or no more than 7.0, or no more than 6.0, or no more than 5.0, or no more than 4.0, or no more than 3.5, or no more than 3.0, or no more than 2.5, or no more than 2.0.

In some embodiments, the aforementioned chemical treatment reduces the color of the fatty acid ester composition on the AOCS-Tintometer Yellow Scale. In some such embodiments, the chemical treatment reduces the color of the fatty acid ester composition such that the composition has a color value on the AOCS-Tintometer Yellow Scale of no more than 50.0, or no more than 35.0.

The chemical treatment can be carried out in any suitable means. For example, in some embodiments, the fatty acid ester composition is contacted multiple times with a decolorizing composition, which may be different in certain instances. For example, in some embodiments, the fatty acid ester composition is contacted separately with an aqueous chlorite solution and an aqueous persulfate solution. In some embodiments, this can be carried out in a series of different contacting events.

The contacting can be carried out in any suitable way. For example, in embodiments where the decolorizing composition is aqueous, it can be desirable, in some such embodiments, to wash the fatty acid ester composition with an amount of the decolorizing composition, e.g., by mixing, extracting, or the like. Any suitable relative amounts of the aqueous decolorizing composition and the fatty acid ester composition can be used. In some embodiments, the weight-to-weight ratio of the aqueous decolorizing composition to the fatty acid ester composition ranges from 1:3 to 20:1, or from 1:2 to 10:1, or from 1:1 to 5:1.

FIG. 1 shows a non-limiting example of a method of removing colored impurities from a fatty acid ester composition 100. The method 100 includes: providing a fatty acid ester composition 101, the composition comprising (a) one or more esters of monobasic fatty acids, (b) one or more esters of dibasic fatty acids, and (c) one or more chromophoric impurities; and chemically treating the fatty acid ester composition 102 to reduce the concentration of at least one of the one or more chromophoric impurities.

Figure 2:
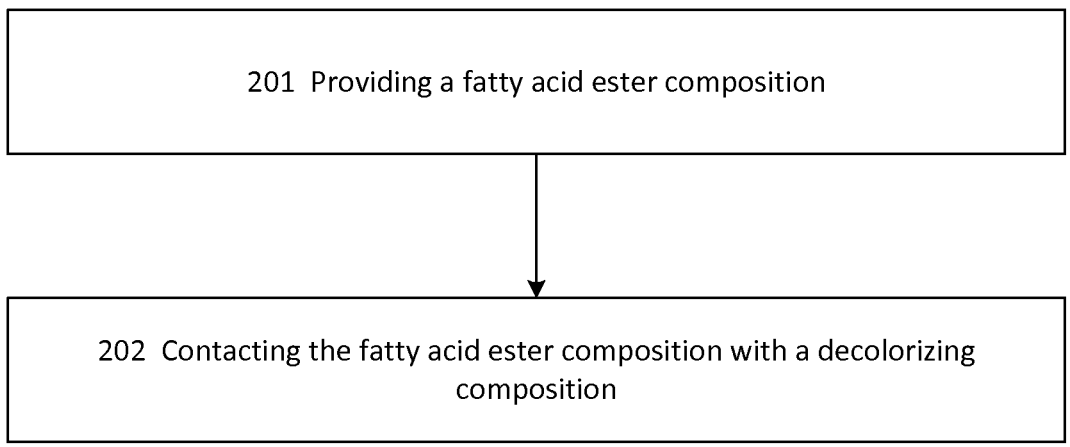
FIG. 2 shows a non-limiting example of a method of removing colored impurities from a fatty acid ester composition, which includes providing a fatty acid ester composition, and contacting the fatty acid ester composition with a decolorizing composition.

FIG. 2 shows a non-limiting example of a method of removing colored impurities from a fatty acid ester composition 200. The method 200 includes: providing a fatty acid ester composition 201, the composition comprising (a) one or more esters of monobasic fatty acids, (b) one or more esters of dibasic fatty acids, and (c) one or more chromophoric impurities; and contacting the fatty acid ester composition with a decolorizing composition 202.

Figure 3:
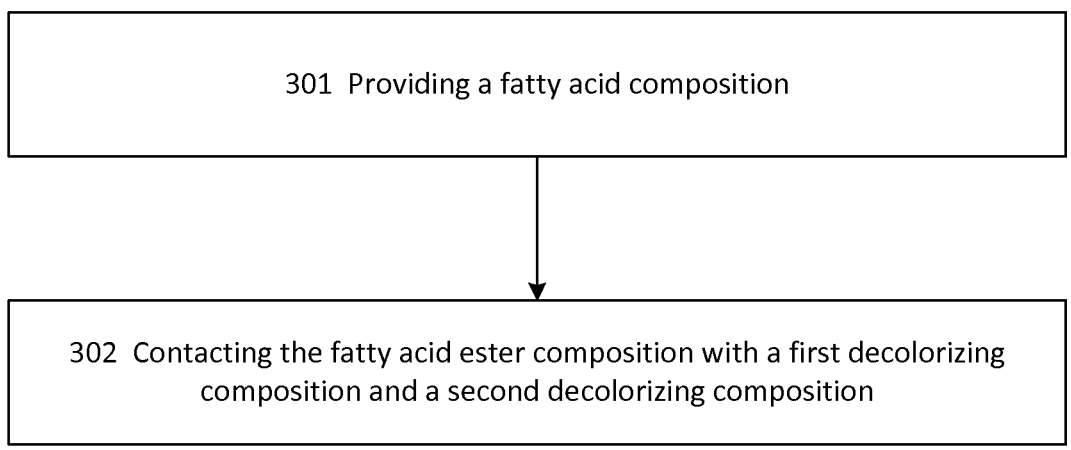
FIG. 3 shows a non-limiting example of a method of removing colored impurities from a fatty acid ester composition, which includes providing a fatty acid ester composition, and contacting the fatty acid ester composition with a first decolorizing composition and a second decolorizing composition.

FIG. 3 shows a non-limiting example of a method of removing colored impurities from a fatty acid ester composition 300. The method 300 includes: providing a fatty acid ester composition 301, the composition comprising (a) one or more esters of monobasic fatty acids, (b) one or more esters of dibasic fatty acids, and (c) one or more chromophoric impurities; and contacting the fatty acid ester composition with a first decolorizing composition and a second decolorizing composition 302, the first and second decolorizing compositions being aqueous compositions that comprise one or more anionic oxidizing agents.

Figure 4:
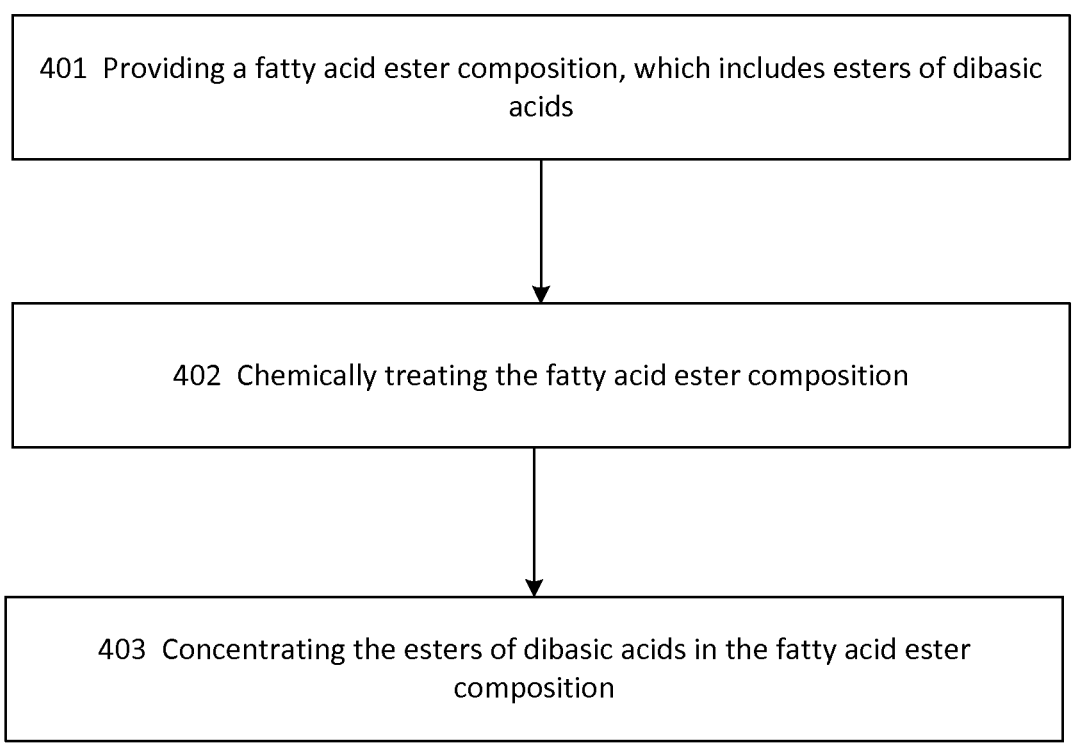
FIG. 4 shows a non-limiting example of a method of removing colored impurities from a fatty acid ester composition, which includes providing a fatty acid ester composition, chemically treating the fatty acid ester composition to reduce the concentration of at least one of the one or more chromophoric impurities, and concentrating one or more esters of dibasic acids in the composition to form a concentrated stream of esters of dibasic acids.

FIG. 4 shows a non-limiting example of a method of removing colored impurities from a fatty acid ester composition 400. The method 400 includes: providing a fatty acid ester composition 401, the composition comprising (a) one or more esters of monobasic fatty acids, (b) one or more esters of dibasic fatty acids, and (c) one or more chromophoric impurities; chemically treating the fatty acid ester composition 402 to reduce the concentration of at least one of the one or more chromophoric impurities; and concentrating the one or more esters of dibasic acids (e.g., 1,18-octadecanedioic acid) 403 to form a concentrated stream of esters of dibasic acids.

Low-Color Fatty Acid Ester Compositions

In certain aspects, the disclosure provides low-color fatty acid ester compositions, the compositions including: one or more esters of monobasic fatty acids; and one or more esters of dibasic fatty acids. In some such embodiments, the composition is substantially free of chromophoric impurities.

In some embodiments, the fatty acid ester composition includes one or more esters of monobasic fatty acids. In some embodiments, the one or more esters of monobasic fatty acids are compounds of formula (III):

$$R^6\text{—}C(\!=\!O)\text{—}O\text{—}R^7 \tag{III}$$

wherein $R^6$ is $C_{6\text{-}36}$ alkyl or $C_{6\text{-}36}$ alkenyl; and $R^7$ is $C_{1\text{-}24}$ alkyl, $C_{2\text{-}24}$ alkenyl, $C_{1\text{-}24}$ heteroalkyl, or $C_{2\text{-}24}$ heteroalkenyl, each of which is optionally substituted with one or more hydroxyl groups.

In some embodiments, $R^6$ is $C_{6\text{-}36}$ alkyl or $C_{6\text{-}36}$ alkenyl. In some embodiments, $R^6$ is $C_{9\text{-}27}$ alkyl or $C_{9\text{-}27}$ alkenyl. In some embodiments, $R^6$ is $C_{9\text{-}25}$ alkyl or $C_{9\text{-}25}$ alkenyl. In some embodiments, $R^6$ is $C_{9\text{-}23}$ alkyl or $C_{9\text{-}23}$ alkenyl. In some such embodiments, $R^6$ is —$(CH_2)_{14}$—$CH_3$, —$(CH_2)_{16}$—$CH_3$, —$(CH_2)_{18}$—$CH_3$, —$(CH_2)_{19}$—$CH_3$, —$(CH_2)_{22}$—$CH_3$, or —$(CH_2)_7$—$CH\!=\!CH$—$(CH_2)_7$—$CH_3$.

In some embodiments, $R^7$ is $C_{1\text{-}12}$ alkyl or $C_{1\text{-}12}$ oxyalkyl, each of which is optionally substituted with one or more hydroxyl groups. In some embodiments, $R^7$ is $C_{1\text{-}6}$ alkyl, which is optionally substituted with one or more hydroxyl groups. In some embodiments, $R^7$ is methyl, ethyl, or isopropyl. In some embodiments, $R^7$ is methyl. In some other embodiments, $R^7$ is a glyceryl group.

In some other embodiments, the one or more esters of monobasic fatty acids are esters of $C_{12\text{-}24}$ monobasic fatty acids. In some embodiments, the one or more esters of monobasic fatty acids are esters of $C_{14\text{-}21}$ monobasic fatty acids. In some embodiments, the one or more esters of monobasic fatty acids are esters of palmitic acid, stearic acid, oleic acid, arachidic acid, heneicosylic acid, lignoceric acid, or mixtures thereof. In some embodiments, the one or more esters of monobasic fatty acids are esters of palmitic acid, stearic acid, or mixtures thereof.

In the aforementioned esters, any suitable alcoholic moiety can be used, including heteroalkyl groups, such as oxyalkyl and glycerides. In some embodiments, the one or more esters of monobasic fatty acids are glyceryl esters of monobasic fatty acids. In some such embodiments, the glyceryl groups of the glyceryl esters of monobasic fatty acids are monoglycerides, diglycerides, triglycerides, or mixtures thereof. In some other embodiments, the one or more esters of monobasic fatty acids are $C_{1-12}$ alkyl esters of monobasic fatty acids. In some such embodiments, the $C_{1-12}$ alkyl esters of monobasic fatty acids are methyl esters of monobasic fatty acids, ethyl esters of monobasic fatty acids, isopropyl esters of monobasic fatty acids, or mixtures thereof. In some further embodiments, the $C_{1-12}$ alkyl esters of monobasic fatty acids are methyl esters of monobasic fatty acids.

In some embodiments, the fatty acid ester composition includes one or more esters of dibasic fatty acids. In some embodiments, the one or more esters of dibasic fatty acids are compounds of formula (IV):

$$R^9\text{---}O\text{---}C(=O)\text{---}R^8\text{---}C(=O)\text{---}O\text{---}R^{19} \quad (IV)$$

wherein $R^8$ is $C_{6-36}$ alkylene or $C_{6-36}$ alkenylene; and $R^9$ and $R^{19}$ are independently $C_{1-24}$ alkyl, $C_{2-24}$ alkenyl, $C_{1-24}$ heteroalkyl, or $C_{2-24}$ heteroalkenyl, each of which is optionally substituted with one or more hydroxyl groups.

In some embodiments, $R^8$ is $C_{6-36}$ alkylene or $C_{6-36}$ alkenylene. In some embodiments, $R^8$ is $C_{8-26}$ alkylene or $C_{8-26}$ alkenylene. In some embodiments, $R^8$ is $C_{8-24}$ alkylene or $C_{8-24}$ alkenylene. In some embodiments, $R^8$ is $C_{8-22}$ alkylene or $C_{8-22}$ alkenylene. In some such embodiments, $R^8$ is —(CH$_2$)$_{16}$—, —(CH$_2$)$_{18}$—, or —(CH$_2$)$_{19}$—.

In some embodiments, $R^9$ and $R^{10}$ are independently $C_{1-12}$ alkyl or $C_{1-12}$ oxyalkyl, each of which is optionally substituted with one or more hydroxyl groups. In some embodiments, $R^9$ and $R^{10}$ are independently $C_{1-6}$ alkyl, which is optionally substituted with one or more hydroxyl groups. In some embodiments, $R^9$ and $R^{10}$ are independently methyl, ethyl, or isopropyl. In some embodiments, $R^9$ and $R^{10}$ are methyl. In some other embodiments, at least one of $R^9$ and $R^{10}$ are independently glyceryl groups.

In some other embodiments, the one or more esters of dibasic fatty acids are esters of $C_{12-24}$ dibasic fatty acids. In some embodiments, the one or more esters of dibasic fatty acids are esters of $C_{14-21}$ dibasic fatty acids. In some embodiments, the one or more esters of dibasic fatty acids are esters of octadecanedioic acid, eicosanedioic acid, heneicosanedioic acid, or mixtures thereof. In some embodiments, the one or more esters of dibasic fatty acids are esters of octadecanedioic acid, heneicosanedioic acid, or mixtures thereof.

In some further embodiments of the aforementioned embodiments, the one or more esters of dibasic fatty acids are one or more monoesters of dibasic fatty acids, one or more diesters of dibasic fatty acids, or mixtures thereof. In some such embodiments, the one or more esters of dibasic fatty acids are one or more diesters of dibasic fatty acids. In some embodiments, the one or more diesters of dibasic fatty acids are glyceryl diesters of dibasic fatty acids. In some such embodiments, the glyceryl groups of the glyceryl diesters of dibasic fatty acids are monoglycerides, diglycerides, triglycerides, or mixtures thereof. In some other embodiments, the one or more diesters of dibasic fatty acids are $C_{1-12}$ alkyl diesters of dibasic fatty acids. In some such embodiments, the $C_{1-12}$ alkyl diesters of dibasic fatty acids are methyl diesters of dibasic fatty acids, ethyl diesters of dibasic fatty acids, isopropyl diesters of dibasic fatty acids, or mixtures thereof. In some embodiments, the $C_{1-12}$ alkyl diesters of dibasic fatty acids are methyl diesters of dibasic fatty acids.

In some embodiments, the fatty acid ester composition contains esters of monobasic acids and esters of dibasic acids.

In such embodiments, the composition can have any suitable ratio of esters of monobasic acids to esters of dibasic acids. In some embodiments, the weight-to-weight ratio the one or more monobasic fatty acids to the one or more dibasic fatty acids ranges from 1:10 to 10:1, or from 1:5 to 5:1, or from 1:3 to 3:1, or from 1:2 to 2:1.

The fatty acid ester composition can also include certain impurities. For example, in instances where the fatty acid ester composition is derived from a natural oil, the composition can contain certain quantities of colored impurities (also referred to as chromophoric impurities) which are present in the plant or animal from which the oil is derived.

In some embodiments, the fatty acid ester composition can include certain chromophoric impurities, such as those that are commonly found in animal or plant sources. For example, in some embodiments the chromophoric impurity is a tetraterpenoid, such as a carotenoid. In some embodiments, the chromophoric impurity is a xanthophyll, a carotene, or a mixture thereof. In some embodiments, the chromophoric impurity is a carotene, such as alpha-carotene, beta-carotene, gamma-carotene, delta-carotene, epsilon-carotene, zeta-carotene, or a mixture thereof. In some embodiments, the chromophoric impurity is beta-carotene.

In some embodiments, the fatty acid ester composition has a low amount of color. For example, in some embodiments, the color of the fatty acid ester composition has a color value on the AOCS-Tintometer Red Scale of no more than 10.0, or no more than 9.0, or no more than 7.6, or no more than 7.0, or no more than 6.0, or no more than 5.0, or no more than 4.0, or no more than 3.5, or no more than 3.0, or no more than 2.5, or no more than 2.0.

In some embodiments, the fatty acid ester composition has a low amount of color. For example, in some embodiments, the color of the fatty acid ester composition has a color value on the AOCS-Tintometer Yellow Scale of no more than 50.0, or no more than 35.0.

Derivation from Renewable Sources

The fatty acid ester compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms (e.g., yeast), and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride. In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. In some further embodiments, the alkene is 2-butene.

Metathesis reactions can provide a variety of useful products. In many instances, it can be desirable to perform certain chemical modifications or certain separations to obtain product streams having certain desired properties. For example, in some embodiments, such as where the ester products of the metathesis are primarily glycerides, it can be desirable to perform a transesterification on the glycerides to convert them to esters of monohydric alcohols. In some such embodiments, this can be accomplished by reacting the glycerides with a monohydric alcohol (e.g., methanol) to obtain such esters (e.g., methyl esters). If the metathesis reaction involved reactions involving esters of monohydric alcohols (e.g., methyl esters), then it may be unnecessary to perform transesterification.

Further, either before and/or after transesterification, if it is performed at all, certain components can be separated from the product stream by suitable means. For example, venting may be sufficient to remove certain shorter-chain olefins. To separate other components of combinations of components, one can use fractional distillation. At a certain point, it may not be cost effective and/or technically feasible to continue with the fractionation, which will leave an unfractionated composition behind. As noted above, this can be referred to as the bottoms or as a bottoms stream. In some embodiments, the fatty acid ester compositions described herein (in any of the above embodiments) include the bottoms stream resulting from the metathesis of a natural oil with a short-chain olefin (e.g., ethylene, propene, 1-butene, or 2-butene). In some further embodiments, the fatty acid ester compositions described herein (in any of the above embodiments) include a composition (or, in some embodiments, consist essentially of a composition) derived from a natural oil by a process that further includes removing at least a portion of the volatile and semi-volatile components from the metathesized product to form a non-volatile metathesized product, e.g., the bottoms stream resulting from the metathesis of a natural oil with a short-chain olefin (e.g., ethylene, propene, 1-butene, or 2-butene). In some embodiments, this bottoms stream is at least partially hydrogenated prior to its incorporation into the fatty acid ester compositions described herein.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The conditions for such metathesis reactions, and the reactor design, and suitable catalysts are as described below with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Further Treatment of the Chemically Treated Fatty Acid Ester Composition

In certain aspects, the disclosure provides methods of separating one or more species from the chemically treated fatty acid ester compositions, for example, to generate streams that have concentrated amounts of certain components of the fatty acid ester composition.

In some embodiments, the fatty acid ester composition includes an amount of esters of 1,18-octadecanedioic acid (ODDA). In some embodiments, the esters of ODDA are glycerides. In some other embodiments, the esters are monohydric alkyl alcohol esters, such as methyl esters.

In embodiments where the ODDA esters are not alkyl esters, it may be desirable to convert the esters to simply esters of monohydric alkyl alcohols, such as methyl esters. This can be carried out in any suitable way. In some embodiments, the ODDA esters (e.g., ODDA glycerides) are contacted with methanol to make methyl esters of ODDA. In some cases, the transesterification solution can contain a mixture of methanol and methoxide (e.g., from sodium methoxide).

The ODDA methyl esters can be separated from other components of the composition (e.g., methyl esters of other acids) by any suitable method. In some embodiments, the methyl esters of ODDA can be separated by fractional distillation, e.g., using any suitable number of stages. In some embodiments, the fractional distillation is carried out in at least 3 stages, or at least 5 stages, or at least 7 stages, e.g., up to about 20 stages. The methyl esters of ODDA can be further purified by washing and/or recrystallization using any suitable solvent, e.g., hexane.

EXAMPLES

The following Examples illustrate certain aspects and embodiments of the compounds, compositions, and methods disclosed herein. The Examples merely illustrate particular embodiments and aspects of the disclosed subject matter, and are not intended to provide substantive limits on the scope of the claimed subject matter.

Example 1

Palm Bottom Esters

A bottoms stream was obtained from the metathesis of palm oil using 1-butene in a bioreactor, which is representative of the bottoms stream from a metathesis biorefinery. Table 1 shows the esters that were present in the composition and their amounts in the composition. The balance of the ingredients are various impurities, olefins, etc. The compounds are identified by the nomenclature: Axx:y, where: A indicates whether it is an ester of a monobasic acid (M) or an ester of a dibasic acid (D); xx indicates the number of carbon atoms; and y indicates the number of carbon-carbon double bonds. About 50 percent by weight of the fatty acid esters are triglycerides.

TABLE 1

| Fatty Acid Ester | Weight Percent |
|---|---|
| M10:0 | 1.01 |
| M12:0 | 0.97 |
| M16:0 | 3.09 |
| M18:0 | 6.56 |
| M18:1 | 2.11 |
| M20:0 | 1.79 |
| M21:0 | 3.05 |
| M22:0 | 0.74 |
| M24:0 | 1.12 |
| D18:0 | 31.01 |
| D20:0 | 1.60 |
| D21:0 | 3.81 |

Example 2

Transesterified Palm Bottom Esters

The palm bottom composition of Example 1 was transesterifies using base-catalyzed transesterification using a 3:1 (wt:wt) mixture of methanol and sodium methoxide, used in excess. Table 2 shows the esters that were present in the composition and their amounts in the composition. The balance of the ingredients are various impurities, olefins, etc. The compounds are identified by the nomenclature: Axx:y, where: A indicates whether it is an ester of a monobasic acid (M) or an ester of a dibasic acid (D); xx indicates the number of carbon atoms; and y indicates the number of carbon-carbon double bonds. The fatty acid esters are methyl esters.

TABLE 2

| Fatty Acid Ester | Weight Percent |
| --- | --- |
| M10:0 | 1.02 |
| M12:0 | 0.62 |
| M16:0 | 24.78 |
| M18:0 | 11.74 |
| M18:1 | 2.63 |
| M20:0 | 1.88 |
| M21:0 | 3.30 |
| M22:0 | 0.70 |
| M24:0 | 1.18 |
| D18:0 | 36.03 |
| D20:0 | 1.78 |
| D21:0 | 3.58 |

Example 3

Decolorization (50-Gram Sample)

A 50-gram sample of the palm bottom composition of Example 1 was obtained. The color of the sample was measured: AOCS-Tintometer Red Scale: 17.7; AOCS-Tintometer Yellow Scale: 70.0. A first decolorizing solution was prepared by dissolving 15 g of sodium persulfate ($Na_2S_2O_8$) in 150 mL deionized water. A second decolorizing solution was prepared by dissolving 15 g of sodium chlorite ($NaClO_2$) in 150 mL of deionized water. The fatty acid ester sample was washed with the first decolorizing solution. The aqueous phase was removed, and then the remaining oily phase was washed with the second decolorizing solution. Following the two washes, a 33.6-gram sample of oil was recovered. During each wash, the pH of the composition was buffered to a pH of 7-8 by the addition of disodium hydrogen phosphate. The color of the recovered sample was measured: AOCS-Tintometer Red Scale: 4.4; AOCS-Tintometer Yellow Scale: 70.0. The same cycle was repeated on the recovered oily sample using 60-mL solutions at the same concentrations. A 16.4-gram oily sample was recovered. The color of the recovered sample was measured: AOCS-Tintometer Red Scale: 2.1; AOCS-Tintometer Yellow Scale: 38.0.

Example 4

Decolorization (100-Gram Sample)

A 100-gram sample of the palm bottom composition of Example 1 was obtained. The color of the sample was measured: AOCS-Tintometer Red Scale: 17.7; AOCS-Tintometer Yellow Scale: 70.0. A first decolorizing solution was prepared by dissolving 60 g of sodium persulfate ($Na_2S_2O_8$) in 600 mL deionized water. A second decolorizing solution was prepared by dissolving 30 g of sodium chlorite ($NaClO_2$) in 300 mL of deionized water. The fatty acid ester sample was washed with the first decolorizing solution. The aqueous phase was removed, and then the remaining oily phase was washed with the second decolorizing solution. Following the two washes, an 89-gram sample of oil was recovered. The color of the recovered sample was measured: AOCS-Tintometer Red Scale: 5.2; AOCS-Tintometer Yellow Scale: 70.0. During the wash, the pH of the composition was buffered to a pH of 7-8 by the addition of disodium hydrogen phosphate. The same cycle was repeated on the recovered oily sample using 580-mL and 290-mL solutions at the same concentrations, respectively. A 75-gram oily sample was recovered. The color of the recovered sample was measured: AOCS-Tintometer Red Scale: 3.2; AOCS-Tintometer Yellow Scale: 70.0. The same cycle was repeated again on the recovered oily sample using 350-mL and 180-mL solutions at the same concentrations, respectively. A 43-gram oily sample was recovered. The color of the recovered sample was measured: AOCS-Tintometer Red Scale: 1.1; AOCS-Tintometer Yellow Scale: 22.0.

Example 5

Decolorization (Comparative)

A 50-gram sample of the palm bottom composition of Example 1 was obtained. The color of the sample was measured: AOCS-Tintometer Red Scale: 17.7; AOCS-Tintometer Yellow Scale: 70.0. A decolorizing solution was prepared by dissolving 15 g of sodium chlorite ($NaClO_2$) in 150 mL of deionized water. The fatty acid ester sample was washed with the decolorizing solution. Following the two wash, a 27.3-gram sample of oil was recovered. The color of the recovered sample was measured: AOCS-Tintometer Red Scale: 6.4; AOCS-Tintometer Yellow Scale: 70.0. The same cycle was repeated on the recovered oily sample using 60-mL solution at the same concentrations. A 10.1-gram oily sample was recovered. The color of the recovered sample was measured: AOCS-Tintometer Red Scale: 4.9; AOCS-Tintometer Yellow Scale: 60.0.

Example 6

Fractional Distillation of Transesterified Palm Bottoms

Vacuum distillation of the transesterified bottoms sample of Example 2 at a pressure of 5 torr (gauge pressure) using a 10-stage column. The quantities of certain components of the various fractions are shown in Table 3. The balance includes other materials, such as various esters and olefins. Values are given in weight percent.

TABLE 3

| Fraction No. | D18:0 | M18:0 | M24:0 | D20:0/D21:0 |
| --- | --- | --- | --- | --- |
| 1 | 59.53 | 18.23 | 0.48 | 0.50 |
| 2 | 74.68 | 4.34 | — | — |
| 3 | 88.17 | — | 1.36 | 1.93 |
| 4 | 83.74 | — | 0.68 | 4.65 |
| 5 | 78.00 | — | 3.05 | 4.78 |
| 6 | 60.00 | 5.37 | — | 0.63 |
| 7 | 68.47 | — | 1.62 | 1.38 |
| Comb. 1-7* | 72.00 | 4.78 | 1.05 | 3.60 |

*Combination of Fractions 1 through 7.

Example 7

Recrystallization of Fractionally Distilled Samples

The methyl esters of ODDA in each of the above 8 fractions (including the combination fraction) was recrystallized in n-hexane. The quantities of ODDA methyl ester of the various recrystallized fractions are shown in Table 4. The balance includes other materials, such as various esters and olefins. Values are given in weight percent.

TABLE 4

| Fraction No. | D18:0 |
| --- | --- |
| 1 | 82 |
| 2 | 85 |
| 3 | 90 |
| 4 | 95 |
| 5 | 89 |
| 6 | 83 |
| 7 | 90 |
| Comb. 1-7 | 94 |

What is claimed is:

1. A method of removing colored impurities from a fatty acid ester composition, the method comprising:
providing a fatty acid ester composition, the composition comprising (a) one or more esters of monobasic fatty acids, (b) one or more esters of dibasic fatty acids, and (c) one or more chromophoric impurities; and
chemically treating the fatty acid ester composition to reduce the concentration of at least one of the one or more chromophoric impurities.

2. The method of claim 1, wherein the monobasic fatty acids are $C_{12-24}$ monobasic fatty acids.

3. The method of claim 1, wherein the monobasic fatty acids are palmitic acid, stearic acid, or mixtures thereof.

4. The method of claim 1, wherein the one or more esters of monobasic fatty acids are glyceryl esters of monobasic fatty acids.

5. The method of claim 1, wherein the one or more esters of monobasic fatty acids are $C_{1-12}$ alkyl esters of monobasic fatty acids.

6. The method of claim 5, wherein the $C_{1-12}$ alkyl esters of monobasic fatty acids are methyl esters of monobasic fatty acids.

7. The method of claim 1, wherein the dibasic fatty acids are $C_{12-24}$ dibasic fatty acids.

8. The method of claim 7, wherein the dibasic fatty acids are octadecanedioic acid, heneicosanedioic acid, or mixtures thereof.

9. The method of claim 8, wherein the one or more esters of dibasic fatty acids are glyceryl esters of dibasic fatty acids.

10. The method of claim 8, wherein the one or more esters of dibasic fatty acids are $C_{1-12}$ alkyl esters of dibasic fatty acids.

11. The method of claim 10, wherein the $C_{1-12}$ alkyl diesters of dibasic fatty acids are methyl diesters of dibasic fatty acids, ethyl diesters of dibasic fatty acids, isopropyl diesters of dibasic fatty acids, or mixtures thereof.

12. The method of claim 11, wherein the $C_{1-12}$ alkyl diesters of dibasic fatty acids are methyl diesters of dibasic fatty acids.

13. The method of claim 1, wherein the chromophoric impurity is a tetraterpenoid.

14. The method of claim 13, wherein the chromophoric impurity is a xanthophyll, a carotene, or a mixture thereof.

15. The method of claim 1, wherein the chemically treating comprises contacting the fatty acid ester composition with a decolorizing composition.

16. The method of claim 15, wherein the decolorizing composition is an aqueous composition, which comprises one or more anionic oxidizing agents.

17. The method of claim 16, wherein the one or more anionic oxidizing agents comprise chlorite anions ($ClO_2^-$), persulfate anions ($S_2O_8^{2-}$, or a combination thereof.

18. The method of claim 15, wherein the chemically treating comprises contacting the fatty acid ester composition with a first decolorizing composition and a second decolorizing composition, the first and second decolorizing compositions being aqueous compositions that comprise one or more anionic oxidizing agents.

19. The method of claim 18, wherein the first decolorizing composition comprises chlorite anions ($ClO_2^-$).

20. The method of claim 18, wherein the second decolorizing composition comprises persulfate anions ($S_2O_8^{2-}$).

* * * * *